(12) United States Patent
Koehler et al.

(10) Patent No.: US 11,925,462 B2
(45) Date of Patent: Mar. 12, 2024

(54) SYSTEM AND METHOD FOR ANALYZING GLUCOSE MONITORING DATA INDICATIVE OF A GLUCOSE LEVEL, AND A COMPUTER PROGRAM PRODUCT

(71) Applicant: Roche Diabetes Care, Inc, Indianapolis, IN (US)

(72) Inventors: Matthias Koehler, Laudenbach (DE); Timm Wiedemann, Mannheim (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 547 days.

(21) Appl. No.: 15/414,177

(22) Filed: Jan. 24, 2017

(65) Prior Publication Data

US 2017/0215774 A1 Aug. 3, 2017

(30) Foreign Application Priority Data

Feb. 2, 2016 (EP) .................................. 16153964

(51) Int. Cl.
| | | |
|---|---|---|
| *A61B 5/145* | (2006.01) | |
| *G16H 10/60* | (2018.01) | |
| *G16H 40/63* | (2018.01) | |
| *A61B 5/00* | (2006.01) | |

(52) U.S. Cl.
CPC ........ *A61B 5/14532* (2013.01); *A61B 5/7275* (2013.01); *A61B 5/742* (2013.01); *G16H 10/60* (2018.01); *G16H 40/63* (2018.01)

(58) Field of Classification Search
CPC .... G16H 10/60; G16H 40/63; A61B 5/15432; A61B 5/7275; A61B 5/742
See application file for complete search history.

(56) References Cited

U.S. PATENT DOCUMENTS

2014/0188400 A1   7/2014   Dunn et al.

OTHER PUBLICATIONS

Matthaei, Assessing the value of the Ambulatory Glucose Profile in clinical practice, 2014, 14, pp. 148-152 (Year: 2014).*
Clarke, Statistical Tools to Analyze Continuous Glucose Monitor Data, 2009, 11, pp. S-45 to S-54 (Year: 2009).*
Vashist, Continuous Glucose Monitoring Systems: A Review, 3, pp. 385-412 (Year: 2013).*
Abbott, FreeStyle Navigator II Continuous Glucose Monitoring System: User's Manual, 2015, pp. 1 to 36 (Year: 2015).*
Pernick, Personal Computer Programs to Assist with Self-Monitoring of Blood Glucose and Self-Adjustment of Insulin Dosage, 1986, Diabetes Care, p. 61-69 (Year: 1986).*
Mazze et al., Ambulatory Glucose Profile: Representation of Verified Self-Monitored Blood Glucose data, 1987, Diabetes Care, 10(1), p. 111-117 (Year: 1987).*
Ramchandani et al., New technologies for diabetes: a review of the present and the future, 2012, International Journal of Pediatric Endocrinology, 2012:28, p. 1-10 (Year: 2012).*
English Translation of European Search Report, EP Application No. 16153964, dated Jul. 14, 2016, 9 pages, Germany.
Mazze, et al., Ambulatory Glucose Profile: Representation of Verified Self-Monitored Blood Glucose Data, Diabetes Care, pp. 111-117, vol. 10, No. 1, 1987.
Bergenstal, et al., Recommendations for Standardizing Glucose Reporting and Analysis to Optimize Clinical Decision Making in Diabetes: The Ambulatory Glucose Profile (AGP), Diabetes Technology & Therapeutics, pp. 198-211, vol. 15, No. 3, 2013.
Rodbard, Interpretation of Continuous Glucose Monitoring Data: Glycemic Variability and Quality of Glycemic Control, Diabetes Technology & Therapeutics, pp. S-55 to S-67, vol. 11, supp. 1, Jun. 2009.
Matthaei, Assessing the Value of the Ambulatory Glucose Profile in Clinical Practice, British Journal of Diabetes and Vascular Disease, pp. 148-152, 2014.
Rodbard, Optimizing Display, Analysis, Interpretation and Utility of Self-Monitoring of Blood Glucose (SMBG) Data for Management of Patients with Diabetes, Journal of Diabetes Science and Technology, Jan. 2007, pp. 62-71, vol. 1, Issue 1.
SINOVO Lt. & Co. KG, SiDiary for Android, 2012, Friedrichsdorf, Germany. 19 pages.

* cited by examiner

*Primary Examiner* — Kaitlyn L Minchella
(74) *Attorney, Agent, or Firm* — Bose McKinney & Evans LLP

(57) ABSTRACT

A system for analyzing glucose monitoring data indicative of a glucose level in a bodily fluid. The system includes an input device, a data processing device, an output device, a display device, and machine readable instructions that are executed by the data processing device, wherein the machine readable instructions cause the data processing device to receive glucose monitoring data via the input device, the glucose monitoring data indicating a glucose level in a bodily fluid sampled for a person at a plurality of sample times over a measurement time period in a glucose level measurement, and comprising a plurality of glucose profiles, each of the glucose profiles comprising a plurality of glucose values assigned to one of the plurality of sample times. Furthermore, a method for analyzing glucose monitoring data indicative of a glucose level in a system is provided.

17 Claims, 7 Drawing Sheets

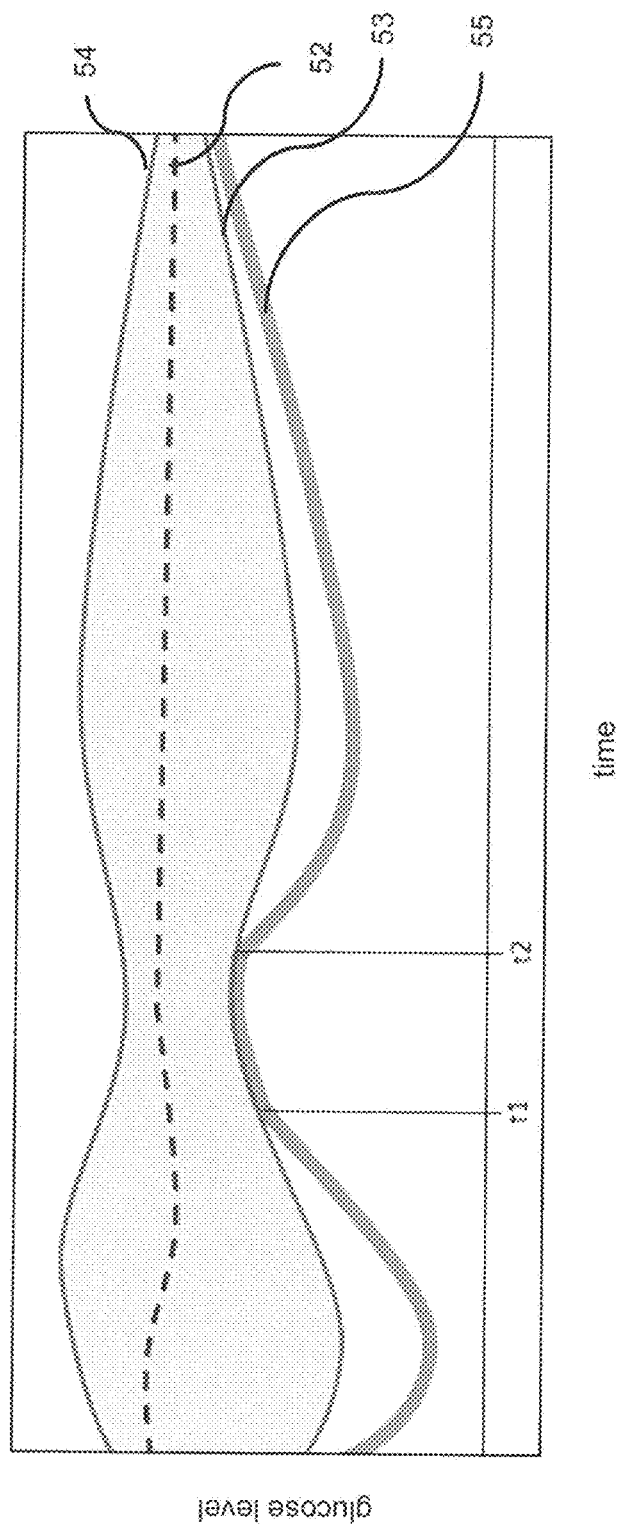

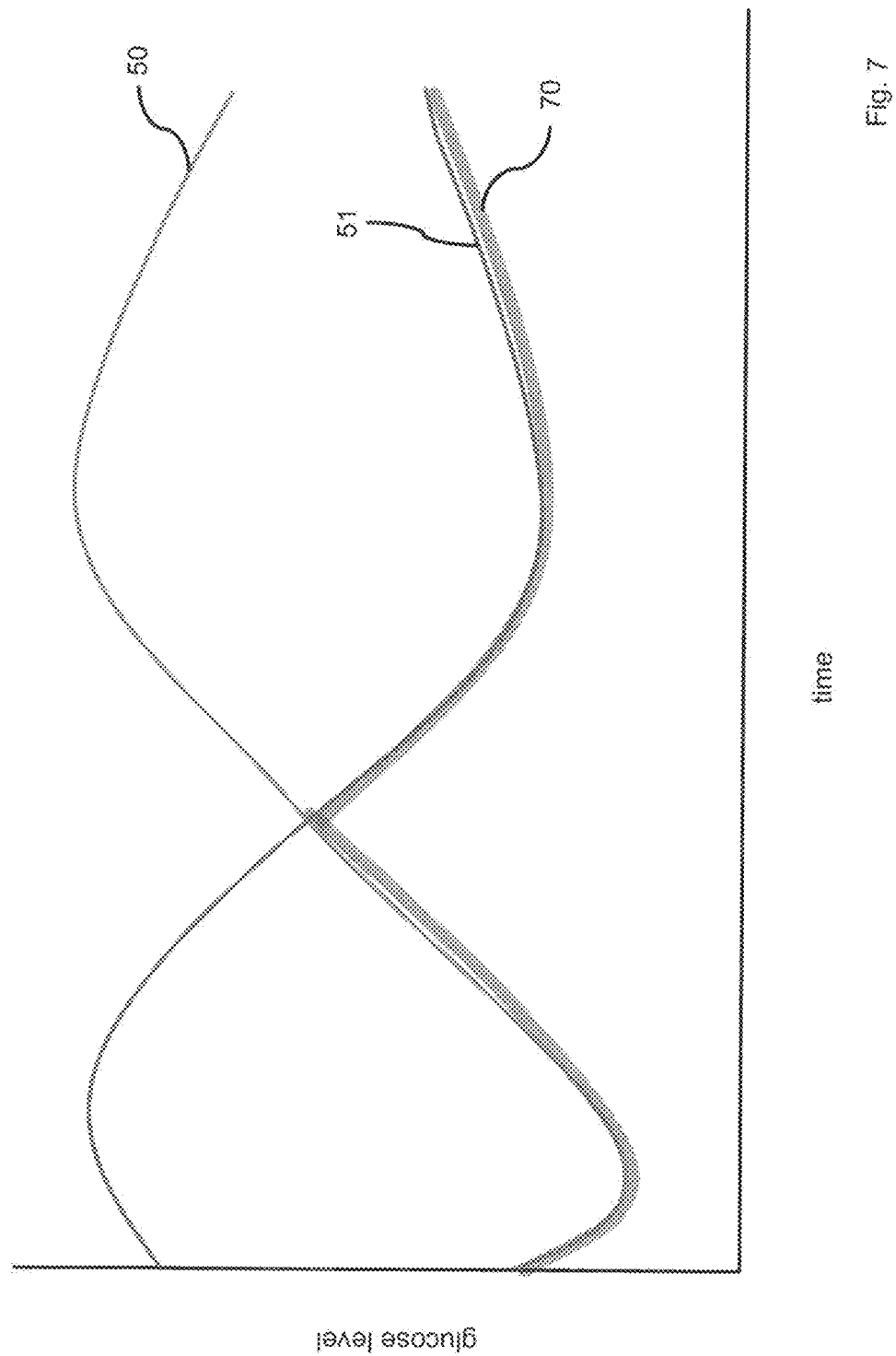

SYSTEM AND METHOD FOR ANALYZING GLUCOSE MONITORING DATA INDICATIVE OF A GLUCOSE LEVEL, AND A COMPUTER PROGRAM PRODUCT

CROSS REFERENCE TO RELATED APPLICATIONS

This application claims priority to EP 16 153 964.8 filed Feb. 2, 2016, the disclosure of which is incorporated herein by reference.

BACKGROUND

1. Technical Field of the Invention

The present disclosure refers to systems and methods for analyzing glucose monitoring data indicative of a glucose level, and a computer program product.

2. Description of the Related Art

Glucose monitoring helps people with diabetes manage the disease and avoid its associated problems. A person can use the results of glucose monitoring to make decisions about food, physical activity, and medications. A common way to check glucose level is performing discontinuous monitoring. Such checking usually involves pricking a fingertip with an automatic lancing device to obtain a blood sample and then using a glucose meter to measure the blood sample's glucose level. Such monitoring may also be referred to as spot monitoring.

As an alternative or in addition continuous glucose monitoring (CGM) may be applied. A system for CGM may use a body sensor inserted under the skin to check glucose levels. The sensor stays in place for several days to weeks and then must be replaced. A transmitter sends information about an analyte value or level indicative of the glucose level via wireless data transmission from the sensor to a monitor device. The user may check blood samples with a glucose meter to program the devices.

An ambulatory glucose profile (AGP) may be determined (Matthaei: "Assessing the value of the Ambulatory Glucose Profile in clinical practice", The British Journal of Diabetes and Vascular Disease; Mazze et al.: "Ambulatory Glucose Profile representation of verified self-monitored blood glucose data", Diabetes Care 1987, 10: 111-117; Bergenstal et al.: "Recommendation for standardizing glucose reporting and analysis to optimize clinical decision making in diabetes: The Ambulatory Glucose Profile (AGP)", Diabetes Technol Ther 2013; 15: 198-211). In a standardized manner the AGP combines inputs from multiple days of collected CGM data and collates them into a single 24-hour period. AGPs may make glycaemic patterns more recognizable.

Referring to Bergenstal et al., in the AGP glucose monitoring presentation data collected over multiple days, e.g. two weeks, are collapsed and plotted according to time (without regard to date) as if they occurred over 24 h, starting and ending at midnight. Smoothed curves representing the median ($50^{th}$), $25^{th}$ and $75^{th}$ (IQR—inter quartile range), and $10^{th}$ and $90^{th}$ frequency percentiles may be depicted in the (24-h) presentation referred to as AGP. At a glance one can observe the time(s) of day when the glucose value is most consistently low or high and when the most variability is occurring (the width of the $25^{th}$ to $75^{th}$ percentile (50% of reading) or $10^{th}$ to $90^{th}$ frequency (80% of readings)) that needs to be addressed. This is an exercise clinicians can do together with patients in a matter of minutes. For instance, without dependence on numbers, formulas, or derived indices, clinicians and patients can quickly become skilled at identifying the risk of hypoglycemia.

SUMMARY

The present disclosure provides improved technologies for analyzing glucose monitoring data indicative of a glucose level in a bodily fluid.

A system and a method are provided for analyzing glucose monitoring data indicative of a glucose level in a bodily fluid. Further, a computer program product is provided. Various alternative embodiments are also disclosed.

According to an aspect, a system for analyzing glucose monitoring data indicative of a glucose level in a bodily fluid is provided. The system comprises an input device, a data processing device, an output device, a display device, and machine readable instructions that are executed by the data processing device. The machine readable instructions cause the data processing device to: receive glucose monitoring data via the input device, the glucose monitoring data indicating a glucose level sampled for a person in a bodily fluid at a plurality of sample times over a measurement time period in a glucose level measurement, and comprising a plurality of glucose profiles, each of the glucose profiles comprising a plurality of glucose values assigned to one of the plurality of sample times; for the plurality of glucose profiles, determine at least one of a minimum glucose value and a maximum glucose value for a selected group or each of the plurality of sample times; provide first display signals representing at least one of the minimum glucose value and the maximum glucose value for the selected group or each of the plurality of sample times; output the first display signals via the output device to the display device; and display a first graphical representation according to the first display signals on the display device.

According to another aspect, a method for analyzing glucose monitoring data indicative of a glucose level in a system is provided. The system comprises a data processing device, an input device, an output device, and a display device. The method comprises: receiving glucose monitoring data via the input device, the glucose monitoring data indicating a glucose level sampled for a person in a bodily fluid at a plurality of sample times over a measurement time period in a glucose level measurement, and comprising a plurality of glucose profiles, each of the glucose profiles comprising a plurality of glucose values assigned to one of the plurality of sample times; for the plurality of glucose profiles, determining at least one of a minimum glucose value and a maximum glucose value for a selected group or each of the plurality of sample times; providing first display signals representing at least one of the minimum glucose value and the maximum glucose value for the selected group or each of the plurality of sample times; outputting the first display signals via the output device to the display device; and displaying a first graphical representation according to the first display signals on the display device.

Further, a computer program product, preferably stored on a storage medium, is configured to perform the method for analyzing glucose monitoring data indicative of a glucose level during operation on a system comprising a data processing device, an input device, an output device, and a display device.

The order of the steps caused by the machine readable instructions and performed by the processing device may be different in the various embodiments.

The glucose monitoring data is a stream of data collected or sampled for a bodily fluid of a person or patient for a plurality of sample times over a measurement time period in a glucose level monitoring. The sample time is a parameter that indicates when, during the measurement time period, the respective glucose value is detected in the glucose level measurement. The term sample time as referred to here may define a fixed time. In an alternative embodiment, for glucose values from different glucose profiles all assigned to the "same sample time" the actual sample times may be spread over a short period of time, e.g. one or several minutes or even an hour. In such case, the sample time for which the glucose values from the different glucose profiles are compared is not a single defined time. Rather, the sample time is a (limited) period of time. For example, such sample time spreading may take place if the glucose monitoring is done on different days.

In an embodiment, a glucose profile comprises a glucose value for each of the plurality of sample times over the measurement time period. Such measurement time period, for example, may be 24 h.

The measurement time period applies to each of the glucose profiles. For example, the plurality of glucose profiles is determined on different days which may be done by sampling the glucose level on each day over the measurement time period.

In the process of determining the minimum glucose value, the glucose values of all glucose profiles assigned to a respective sample time may be considered for determining the glucose value indicating the lowest glucose level at the specific sample time. Such determination may be done for the selected group or each of the plurality of sample times providing a plurality of minimum glucose values. For example, such plurality of minimum glucose values may be determined for all sample times over a 24 h time period.

With regard to determining the minimum glucose value only for the selected group of the plurality of sample times, all sample times may be selected for which a hypo glucose value is determined.

The machine readable instructions may cause the data processing device to provide continuous first display signals representing a continuous curve for at least one of the minimum glucose value and the maximum glucose value for the selected group or each of the plurality of sample times. The first display signals may be representing a continuous line to be presented on the display device.

The machine readable instructions may cause the data processing device to provide discontinuous first display signals representing a discontinuous curve provided with separated curve segments for at least one of the minimum glucose value and the maximum glucose value for the selected group or each of the plurality of sample times. The discontinuous first display signals may be representing an interrupted line to be presented on the display device. There may be segments or intervals separated from each other. As an alternative or in addition, isolated points may be presented on the display device.

The machine readable instructions may cause the data processing device to determine an ambulatory glucose profile for the plurality of glucose values of the plurality of glucose profiles, and provide the first display signals further representing the ambulatory glucose profile. The ambulatory glucose profile which is also be referred to as AGP may represent the median curve, the 25th and 75th percentile curves and the 10th and 90th percentile curves for glucose values (glucose profiles) collected over a period of time, e.g. two weeks. The AGP may be a 24 h AGP (24 h ambulatory glucose profile).

The machine readable instructions may cause the data processing device to substitute, for one or more sample times, (i) the minimum glucose value by a pre-determined low glucose value if the minimum glucose value is determined higher than the pre-determined low glucose value, and/or (ii) the maximum glucose value by a pre-determined high glucose value if the maximum glucose value is determined smaller than the pre-determined high glucose value. A substitution may be performed prior to providing the first display signals. At least one of a pre-determined low glucose value and the pre-determined high glucose value may correspond to a percentile of the plurality of glucose values assigned to the plurality of glucose profiles. For example, a 10% percentile and/or a 90% percentile may be applied.

The machine readable instructions may cause the data processing device to provide second display signals. The second display signals are representing the plurality of glucose profiles, output the second display signals via the output device to the display device, and display a second graphical representation according to the second display signals on the display device. In this embodiment, in addition to a graphical representation caused by the first display signals, the plurality of glucose profiles is to be presented on the display device. A graphical line representation may be provided.

The machine readable instructions may cause the data processing device to provide third display signals, the third display signals representing a glucose threshold value, output the third display signals via the output device to the display device, and display a third graphical representation according to the third display signals on the display device. The glucose threshold value may be a pre-determined glucose threshold value which may be determined by a user input. It may indicate a glucose level which shall not be crossed by the (e.g. continuous) glucose level. A graphical line representation may be provided.

The machine readable instructions cause the data processing device to provide fourth display signals, the fourth display signals representing a target range for the monitoring glucose level, output the fourth display signals via the output device to the display device, and display a fourth graphical representation according to the fourth display signals on the display device. The target range may be represented by one or more graphical lines which are continuously or discontinuously represented on the display device. The target range may be defined in response to a user input.

The machine readable instructions may cause the data processing device to receive continuous glucose monitoring data via the input device, the continuous glucose monitoring data indicating a glucose level for the person sampled in the bodily fluid at the plurality of sample times over a measurement time period in a continuous glucose level measurement.

The glucose monitoring data may be analyte monitoring data providing a stream of data collected or sampled for a person or patient for a plurality of sample times over a measurement time period in an analyte level monitoring, the analyte level being indicative of a glucose level in a bodily fluid.

With regard to a glucose measurement or monitoring, a glucose level or value may be determined by analyzing a blood sample via e.g. spot monitoring, and, as an alternative or in addition, by continuous glucose monitoring (CGM) via a fully or partially implanted sensor. In general, in the context of CGM a glucose value or level in a bodily fluid may be determined. The analyte value may be, e.g., subcutaneously measured in an interstitial fluid. CGM may be implemented as a nearly real-time or quasi-continuous monitoring procedure frequently or automatically providing/updating analyte values without user interaction.

The various embodiments referred to above with regard to the system may apply to the method for automatically analyzing continuous glucose monitoring data indicative of a glucose level in the same way.

BRIEF DESCRIPTION OF THE DRAWINGS

The above mentioned and other features of this invention, and the manner of attaining them, will become more apparent and the invention itself will be better understood by reference to the following description of embodiments of the invention taken in conjunction with the accompanying drawings, wherein:

FIG. 6 is a graphical representation of a selected group of curves from FIG. 5 and a minimum line; and FIG. 7 is a graphical representation of another selected group of curves from FIG. 5 and a minimum line.

Figure 1:
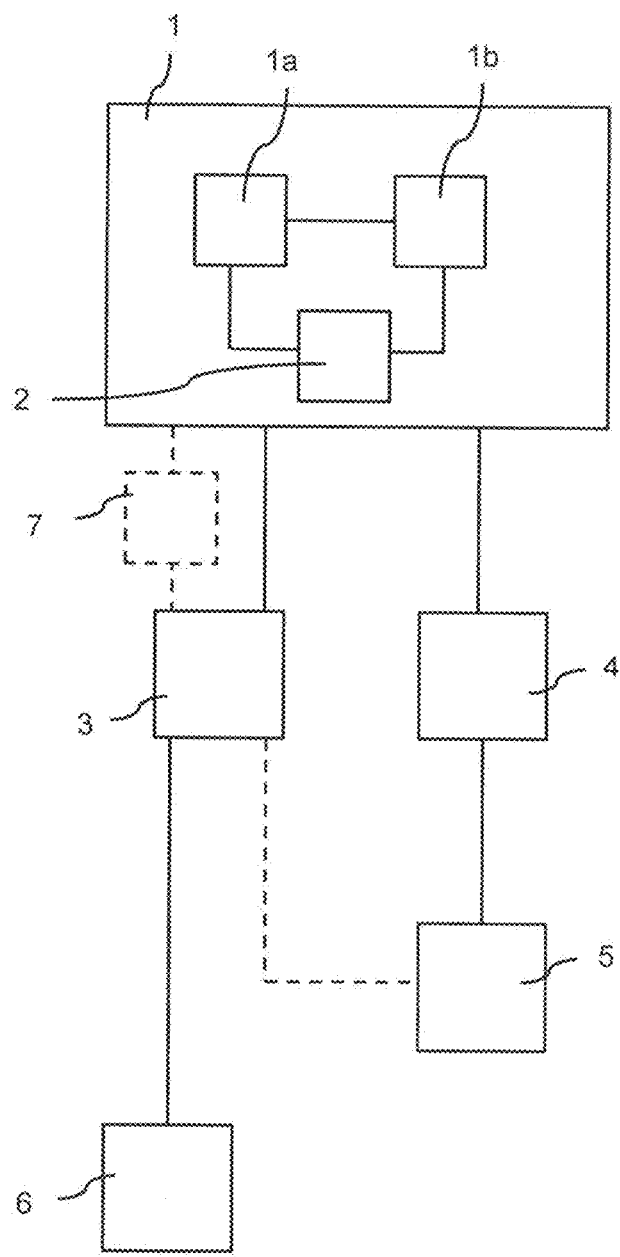
FIG. 1 is a schematic representation of a system for automatically analyzing continuous glucose monitoring data indicative of a glucose level.

Corresponding reference characters indicate corresponding parts throughout the several views. Although the exemplification set out herein illustrates embodiments of the invention, in several forms, the embodiments disclosed below are not intended to be exhaustive or to be construed as limiting the scope of the invention to the precise forms disclosed.

DETAILED DESCRIPTION

FIG. 1 generally depicts an embodiment of a system for automatically analyzing continuous glucose monitoring data indicative of a glucose level. The system generally comprises a processing device 1 provided with one or more processors 1a, 1b. Also, the processing device 1 comprises a memory 2 for storing machine readable instructions. The processing device 1 is connected to an input device 3 configured to receive electronic data and an output device 4 configured for outputting electronic data. The input device 3 and the output device 4 may be implemented integrally with processing device 1.

A human machine interface 5 is communicably coupled to the output device 4 and, optionally, the input device 3 and the output device 4.

Machine readable instructions are provided that are executed by the processing device 1 for analyzing glucose monitoring data indicative of a glucose level. Various embodiments of the system and methods for analyzing glucose monitoring data indicative of a glucose level will be described in more detail herein.

The one or more processors 1a, 1b may be a controller, an integrated circuit, a microchip, a computer, or any other computing device capable of executing machine readable instructions. The memory 2 may be RAM, ROM, a flash memory, a hard drive, or any device capable of storing machine readable instructions.

In the embodiments described herein, the one or more processors 1a, 1b may be integral with a single component of the system. However, it is noted that the one or more processors 1a, 1b may be separately located within discrete components such as, for example, a glucose meter, a medication delivery device, a mobile phone, a portable digital assistant (PDA), a mobile computing device such as a laptop, a tablet, or a smart phone, a desktop computer, or a server e.g. via a cloud or web based technologies and communicatively coupled with one. It is to be appreciated that in at least one embodiment of the mobile computing device which is useful with one or more embodiments disclosed herein, such a device may include a touch screen and the computing ability to run computational algorithms and/or processes, such as those disclosed herein, and applications, such as an electronic mail program, a calendar program for providing a calendar, as well as provide cellular, wireless, and/or wired connectivity and one or more of the functions of a glucose meter, a digital media player, a digital camera, a video camera, a GPS navigation unit, and a web browser that can access and properly display web pages. Accordingly, the system may include a plurality of components each having one or more processors 1a, 1b that are communicatively coupled with one or more of the other components. Thus, the systems may utilize a distributed computing arrangement to perform any of the machine readable instructions described herein.

The system further comprises the human machine interface 5 communicatively coupled to the processing device 1 for receiving signals from the output device 4 and presenting graphical, textual and/or auditory information. The human machine interface 5 may include an electronic display such as, for example, a liquid crystal display, thin film transistor display, light emitting diode display, a touch screen, or any other device capable of transforming signals from a processor into an optical output, or a mechanical output, such as, for example, a speaker, a printer for displaying information on media, and the like.

Embodiments of the present disclosure also comprise machine readable instructions that includes logic or an algorithm written in a programming language such as, e.g., machine language that may be directly executed by the processor, or assembly language, object-oriented programming (OOP), scripting languages, microcode, etc., that may be compiled or assembled into machine readable instructions and stored on a machine readable medium. Alternatively, the logic or algorithm may be written in a hardware description language (HDL), such as implemented via either a field-programmable gate array (FPGA) configuration or an application-specific integrated circuit (ASIC), and their equivalents. Accordingly, the machine readable instructions may be implemented in any conventional computer programming language, as pre-programmed hardware elements, or as a combination of hardware and software components. Moreover, machine readable instructions can be distributed over various components that are communicatively coupled such as, for example, via wires, via a wide area network, via a local area network, via a personal area network, and the like. Thus, any components of the system can transmit signal over the Internet or World Wide Web).

Referring still to FIG. 1, the system may optionally include a body sensor 6 communicatively coupled to the processing device 1 through the input device 3 for providing biological data indicative of properties of an analyte. The body sensor 6 may be coupled via the input device 3 or via the input device 3 and an additional intermediate device 7 to the processing device 1. The input device 3 may be configured to receive raw data from the body sensor 6 and processing them into glucose measurement data and transmitting the glucose measurement data to the processing device 1 directly or indirectly via the intermediate device 7. The input device 3 may be configured to control data transmission between the body sensor 6 and the processing device 1, optionally through the intermediate device 7.

Further, in an alternative embodiment, by the input device 3 a remote control for the body sensor 6 may be implemented. The remote controlling may transmit control signals for turning on and/or turning off sensor detection. In addition or as an alternative, the input device 3, if implementing the remote controller, may trigger data transmission from the body sensor 6 to the input device 3.

In one embodiment, the body sensor 6 is a glucose sensor configured to detect glucose levels (e.g., glucose concentrations) when placed just under the skin of a patient. For example, the body sensor 6 can be a disposable glucose sensor that is worn under the skin for a few days until replacement is needed. As is noted above, the body sensor 6 can be communicatively coupled with the processing device 1, which can be located within various discrete components. Accordingly, in the case of a glucose sensor, the body sensor 6 can be communicatively coupled with, for example, a smart glucose meter, or a medication delivery device and can provide ambulatory CGM data, i.e., glucose data that is sampled continuously throughout the lifetime of the sensor.

According to the embodiments described herein, the one or more processors 1a, 1b of the processing device 1 can execute machine readable instructions to automatically analyze continuous glucose monitoring data indicative of a glucose level.

Figure 2:
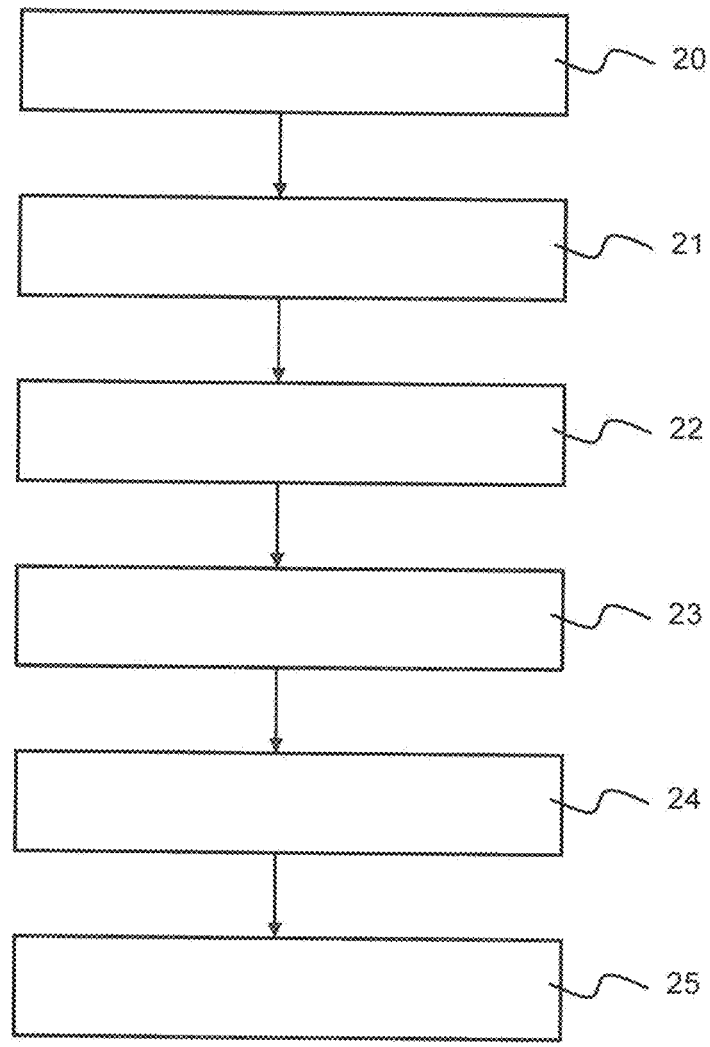
FIG. 2 is a schematic block diagram of a method for automatically analyzing continuous glucose monitoring data indicative of a glucose level.

FIG. 2 shows a schematic representation of a block diagram with regard to a method for analyzing glucose monitoring data indicative of a glucose level. Continuous or discontinuous glucose monitoring data may be analyzed. In step 20, glucose monitoring data are received in the data processing device 1 via the input device 3. The glucose monitoring data are indicating a glucose level sampled for a person at a plurality of sample times over a measurement time period in a continuous or a discontinuous glucose level measurement. Further, the glucose monitoring data comprise a plurality of glucose profiles, each of the glucose profiles comprising a plurality of glucose values assigned to one of the plurality of sample times. For example, the glucose profiles each may cover a time period of 24 h which is the measurement time period.

In step 21, at least one of a minimum glucose value and a maximum glucose value is determined for a selected group or each of the plurality of sample times. For the plurality of glucose profiles, the glucose values at the sample times are analyzed to determine at least one of the minimum glucose value and the maximum glucose value.

An ambulatory glucose profile is determined for the plurality of glucose values of the plurality of glucose profiles in an optional step 22.

In step 23, first display signals are generated, the first display signals representing at least one of the minimum glucose value and the maximum glucose value for the selected group or each of the plurality of sample times. In addition, first display signals may be representing the ambulatory glucose profile.

According to steps 24 and 25, the first display signals are outputted via the output device 4 to the display device of the human machine interface 5, and a first graphical representation according to the first display signals is shown on the display device. For example, a respective graphical curve may be presented for the ambulatory glucose profile and at least one of the minimum glucose value and the maximum glucose value for the selected group or each of the plurality of sample times.

Figure 3:
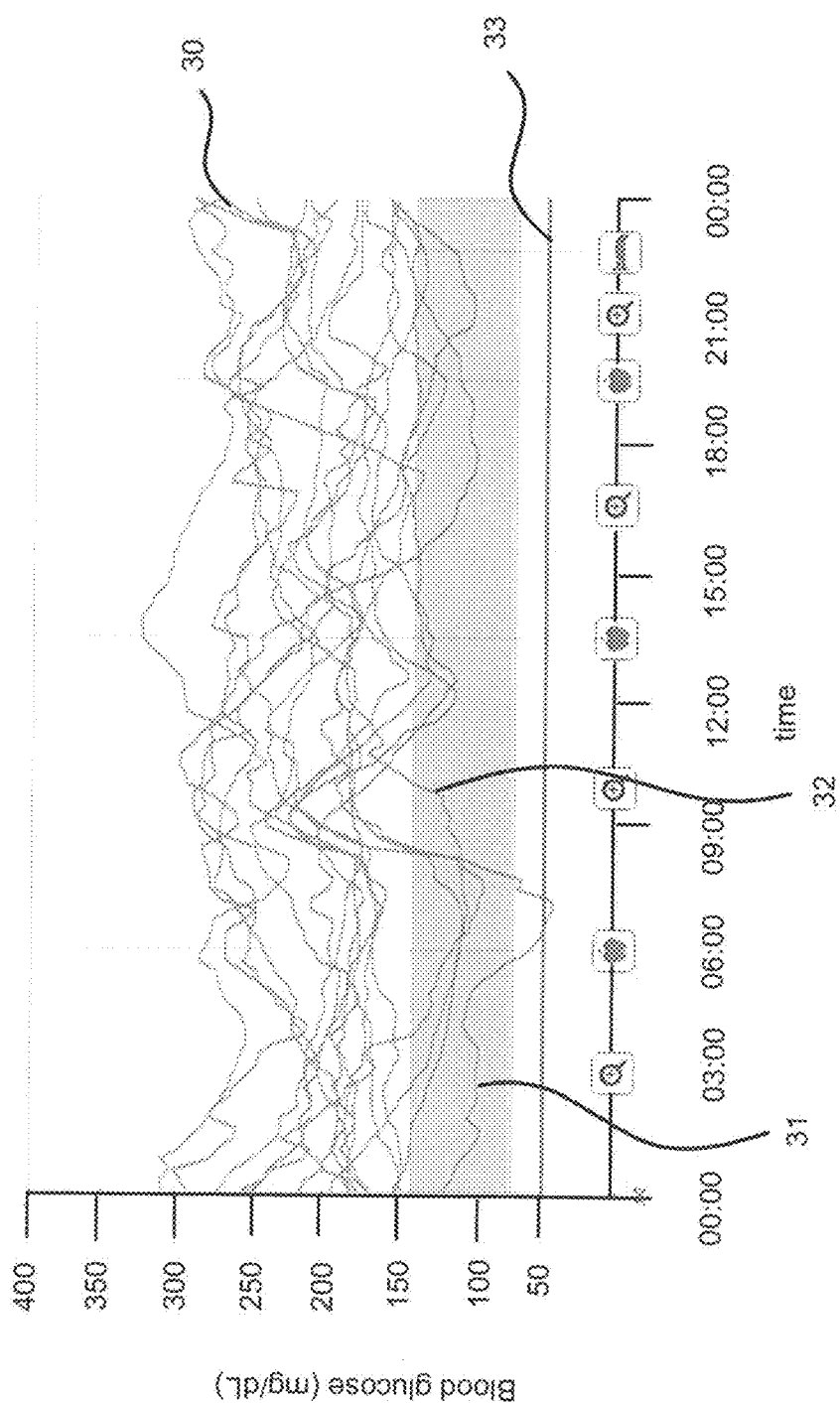
FIG. 3 is a graphical representation of a plurality of curves representing individual continuous glucose monitoring data over a time period of 24 h.

FIG. 3 shows a graphical representation of a plurality of curves 30 representing a plurality of glucose profiles based on continuous glucose monitoring (CGM) data sampled over a measurement time period of 24 h. From FIG. 3 it can be seen that at different sample times different glucose profiles provide for the minimum glucose value. For example, at the sample time of 3 a.m. a first glucose profile 31 provides for the minimum glucose value. At the sample time of 9 a.m., another glucose profile 32 provides for the minimum glucose value. A similar situation applies to the maximum glucose value at different sample times. Also, a hypoglycaemia (hypo) boundary 33 is depicted in FIG. 3.

Figure 4:
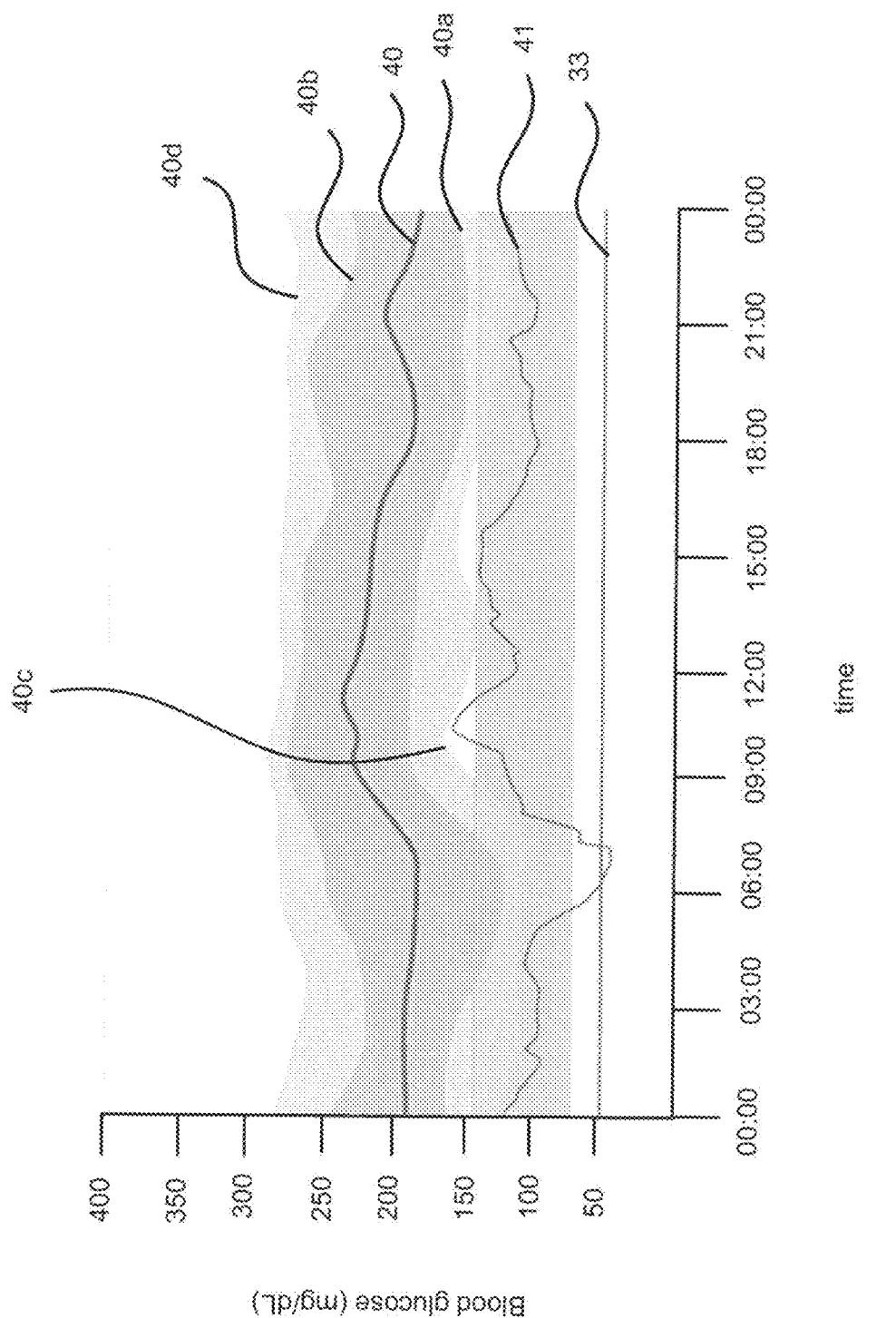
FIG. 4 is a graphical representation of an ambulatory glucose profile (AGP) determined for the plurality of curves in FIG. 3 and a curve representing the minimum glucose value for the plurality of curves in FIG. 3 over the time period of 24 h.

FIG. 4 shows an ambulatory glucose profile (AGP) determined for the plurality of glucose profiles 30 in FIG. 3. The median curve is represented by curve 40. Further curves 40a, 40b of the AGP represent the 25% and the 75% percentile curves, respectively. Further the 10% and the 90% percentiles are depicted by curves 40c and 40d, respectively. In addition, the curve 41 is displayed which represents, for each sample time, the minimum glucose value with regard to all curves of the plurality of glucose profiles 30.

In the representation of CGM data by means of the so-called ambulatory glucose profile, the data are presented in a simplified standard day report (standard day, modal day, overlay), wherein instead of the individual curves (e.g. one curve per day) the median ($50^{th}$) and the 10, 25, 75, 90% ($10^{th}$, $25^{th}$, $75^{th}$, $90^{th}$) percentiles may be displayed.

By the curve 41 the distance from the hypo boundary 33 during non-hypo times is displayed. If, for example, median and percentiles lie significantly above a target region for the entire day and no hypos are present, a physician does not know whether the insulin dose (e.g. the basal rate) may be raised overall since there could be outliers downwards as far as just above the hypo boundary which could result in a hypo if the insulin is raised. By displaying the curve or line 41 representing the minimum glucose values at the sample times, the physician has confirmation that there were no outliers downwards and he can safely increase the basal rate. Or he sees that there was an outlier and he must be careful.

Figure 5:
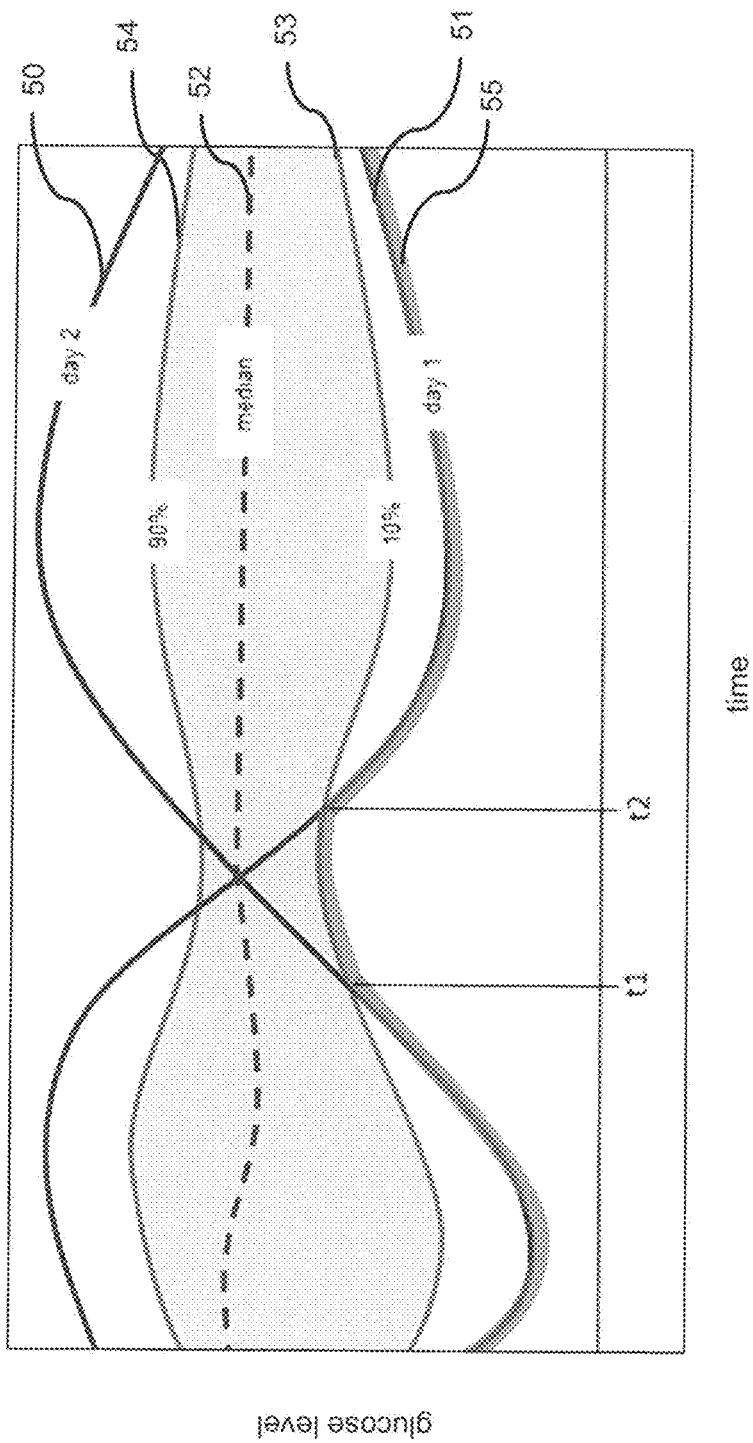
FIG. 5 is a graphical representation of a of an AGP together with additional curves.

FIG. 5 shows a schematic representation of a median curve, 10th and 90th percentile curves (25th and 75th percentile curves are not depicted here in this reduced form of an AGP). Glucose profile 51 for day 1, and another glucose profile 50 for day 2 are depicted in addition. According to the embodiment in FIG. 5, the reduced form of an AGP is provided with the median curve 52, the 10% percentile 53, and the 90% percentile 54. Further, a minimum line 55 is shown. The minimum line 55 follows the lowest glucose values, i.e. day 2 in the first part (time T<t1) and day 1 in the later part (time T>t2). However, from time t1 to t2 the 10% percentile 53 is lower than the lowest glucose value of the glucose profiles depicted 50, 51, therefore, for times t1 to t2 the minimum line 55 follows the 10% percentile 53.

FIG. 6 shows a graphical representation of a selected group of curves from FIG. 5. In addition the minimum line is depicted by curve 55. FIG. 7 shows the glucose profiles 50 and 51, and the minimum line 70 (in this case no substitution of the minimum glucose value by a pre-determined low glucose value was made).

In order to calculate the percentiles, averaging is usually performed over a period of time in order to have a statistically significant number of data, e.g. all the data of all the days are taken over 2 hours and median and percentiles are calculated from this. The IDC (International Diabetes Center) recommends 2 h, but 1 h or 30 min is also acceptable. The periods of time can lie next to one another (8 to 10, 10 to 12 etc.) or be determined as a moving average (8 to 10, 8:01 to 10:01, 8:02 to 10:02 etc.). As soon as averaging is performed over a period of time, with strongly dynamic curve profiles of the CGM data, the curve or line representing the minimum glucose values at the sample times can intersect or cross the percentiles. If only the values at a specific time were always taken, the minimum would naturally always be below the 10% line. Then, however the number of measured glucose values would then not be statistically significant, e.g. for an AGP over seven days there is then only seven values per minute from which 10 or 90% percentiles are difficult to calculate. When the curve or line representing the minimum glucose values at the sample times intersects the percentiles, this is formally correct but is confusing for the user. One possibility for solving this problem is to always draw the minimum line as the lowest line, i.e. as soon as the curve or line representing the minimum glucose values at the sample times would intersect the 10% percentile, it runs along the 10% line, otherwise it runs as calculated, i.e. it always displays the region of the lowest values.

While this invention has been described as having an exemplary design, the present invention may be further modified within the spirit and scope of this disclosure. This application is therefore intended to cover any variations, uses, or adaptations of the invention using its general principles.

What is claimed is:

1. A method for analyzing glucose monitoring data, comprising:
   using a system which includes:
      a data processing device; and
      a display device, to perform the steps of:
         receiving glucose monitoring data, the glucose monitoring data:
            indicating a glucose level sampled from a bodily fluid of a person at a plurality of sample times over a measurement time period in a glucose level measurement; and
            comprising a plurality of glucose profiles, each of the glucose profiles comprising a plurality of glucose values each assigned to one of the plurality of sample times;
         for the plurality of glucose profiles, determining a minimum glucose value and a maximum glucose value for each of a selected group of sample times or each of the plurality of sample times, wherein the glucose monitoring data includes minimum glucose values higher than a pre-determined low glucose value and maximum glucose values smaller than a pre-determined high glucose value;
         providing first display signals representing the minimum glucose value aid the maximum glucose value for each of the selected group of sample times or each of the plurality of sample times in the form of a curve;
         outputting the first display signals to the display device;
         displaying a first graphical representation according to the first display signals on the display device; and
         substituting, for one or more samples times in the curve representing the minimum glucose value and the curve representing the maximum glucose value for each of the selected group of sample times or each of the plurality of samples times:
            the minimum glucose value by the pre-determined low glucose value when the minimum glucose value is determined higher than the pre-determined low glucose value; and
            the maximum glucose value by the pre-determined high glucose value when the maximum glucose value is determined smaller than the pre-determined high glucose value,
         wherein the first graphical representation includes:
            i) a minimum line which includes the curve representing the minimum glucose value for each of the selected group of sample times or each of the plurality of sample times and the pre-determined low glucose value; and
            ii) a maximum line which includes the curve representing the maximum glucose value for each of the selected group of sample times or each of the plurality of sample times and the pre-determined high glucose value; and
      making a decision to increase a basal rate dosage of insulin to the person based upon a review of the first graphical representation by examining the minimum line and determining that there are no outliers below a hypoglycemic boundary, and administering the increased dosage to the person.

2. The method according to claim 1, wherein the first display signals represent a continuous curve for at least one of the minimum glucose value and the maximum glucose value for each of the selected group of sample times or each of the plurality of sample times.

3. The method according to claim 2 further comprising:
   determining an ambulatory glucose profile for the plurality of glucose values of the plurality of glucose profiles; and
   providing the first display signals further representing the ambulatory glucose profile.

4. The method according to claim 2 further comprising:
   providing second display signals, the second display signals representing the plurality of glucose profiles;
   outputting the second display signals to the display device; and
   displaying a second graphical representation according to the second display signals on the display device.

5. The method according to claim 1 wherein the first display signals represent a discontinuous curve provided with separated curve segments for at least one of the minimum glucose value and the maximum glucose value for each of the selected group of sample times or each of the plurality of sample times.

6. The method according to claim 5 further comprising:
   determining an ambulatory glucose profile for the plurality of glucose values of the plurality of glucose profiles; and providing the first display signals further representing the ambulatory glucose profile.

7. The method according to claim 1 further comprising:
determining an ambulatory glucose profile for the plurality of glucose values of the plurality of glucose profiles; and
providing the first display signals further representing the ambulatory glucose profile.

8. The method according to claim 1:
providing second display signals, the second display signals representing the plurality of glucose profiles;
outputting the second display signals to the display device; and
displaying a second graphical representation according to the second display signals on the display device.

9. The method according to claim 8 further comprising:
providing third display signals, the third display signals representing a glucose threshold value;
outputting the third display signals to the display device; and
displaying a third graphical representation according to the third display signals on the display device.

10. The method according to claim 9 further comprising:
providing fourth display signals, the fourth display signals representing a target range for the glucose levels of the glucose monitoring data;
outputting the fourth display signals to the display device; and
displaying a fourth graphical representation according to the fourth display signals on the display device.

11. The method according to claim 1 further comprising:
providing second display signals, the second display signals representing a glucose threshold value;
outputting the second display signals to the display device; and
displaying a second graphical representation according to the second display signals on the display device.

12. The method according to claim 1 further comprising:
providing second display signals, the second display signals representing a target range for the glucose levels of the glucose monitoring data;
outputting the second display signals to the display device; and
displaying a second graphical representation according to the fourth display signals on the display device.

13. The method according to claim 1 wherein the glucose monitoring data analyzed by the system and received by the data processing device is continuous glucose monitoring data, the continuous glucose monitoring data indicating a glucose level sampled from the bodily fluid of the person at the plurality of sample times over a measurement time period in a continuous glucose level measurement.

14. The method according to claim 1 wherein the step of administering the dosage to the person is performed with a medication delivery device communicatively coupled with the data processing device.

15. A method for analyzing glucose monitoring data, comprising:
using a system which includes:
a data processing device; and
a display device, to perform the steps of:
receiving glucose monitoring data, the glucose monitoring data:
indicating a glucose level sampled from a bodily fluid of a person at a plurality of sample times over a measurement time period in a glucose level measurement; and
comprising a plurality of glucose profiles, each of the glucose profiles comprising a plurality of glucose values each assigned to one of the plurality of sample times;
for the plurality of glucose profiles, determining a minimum glucose value and a maximum glucose value for each of a selected group of sample times or each of the plurality of sample times, wherein the glucose monitoring data includes minimum glucose values higher than a pre-determined low glucose value and maximum glucose values smaller than a pre-determined high glucose value;
providing first display signals representing the minimum glucose value aid the maximum glucose value for each of the selected group of sample times or each of the plurality of sample times in the form of a curve;
outputting the first display signals to the display device;
displaying a first graphical representation according to the first display signals;
determining an ambulatory glucose profile for the plurality of glucose values of the plurality of glucose profiles, wherein the first display signals further represent the ambulatory glucose profile and the ambulatory glucose profile represented by the first display signals consists of percentile curves for glucose values; and
substituting, for one or more sample times in the curve representing the minimum glucose value and the curve representing the maximum glucose value for each of the selected group of sample times or each of the plurality of sample times:
the minimum glucose value by the pre-determined low glucose value when the minimum glucose value is determined higher than the pre-determined low glucose value; and
the maximum glucose value by the pre-determined high glucose value when the maximum glucose value is determined smaller than the pre-determined high glucose value,
wherein the first graphical representation includes:
i) a minimum line which includes the curve representing the minimum glucose value for each of the selected group of sample times or each of the plurality of sample times and the pre-determined low glucose value; and
ii) a maximum line which includes the curve representing the maximum glucose value for each of the selected group of sample times or each of the plurality of sample times and the pre-determined high glucose value; and
making a decision to increase a basal rate dosage of insulin to the person based upon a review of the first graphical representation by examining the minimum line and determining that there are no outliers below a hypoglycemic boundary, and administering the increased dosage to the person.

16. The method according to claim 15 wherein the step of administering the dosage to the person is performed with a medication delivery device communicatively coupled with the data processing device.

17. The method according to claim 15, wherein the first graphical representation of glucose monitoring data on the display device is limited to the minimum line, the maximum line, and the ambulatory glucose profile; and wherein the first graphical representation is the only graphical representation of glucose monitoring data displayed by the display device when displaying the first graphical representation of glucose monitoring data on the display device.

\* \* \* \* \*

UNITED STATES PATENT AND TRADEMARK OFFICE
CERTIFICATE OF CORRECTION

| | |
|---|---|
| PATENT NO. | : 11,925,462 B2 |
| APPLICATION NO. | : 15/414177 |
| DATED | : March 12, 2024 |
| INVENTOR(S) | : Koehler et al. |

It is certified that error appears in the above-identified patent and that said Letters Patent is hereby corrected as shown below:

In the Claims

Column 9, Line 67, Claim 1, "aid" should be --and--.

Column 12, Line 14, Claim 15, "aid" should be --and--.

Signed and Sealed this
Sixteenth Day of April, 2024

Katherine Kelly Vidal
*Director of the United States Patent and Trademark Office*